March 5, 1974 R. KORDES Plant Pat. 3,509
ROSE PLANT
Filed Sept. 7, 1972
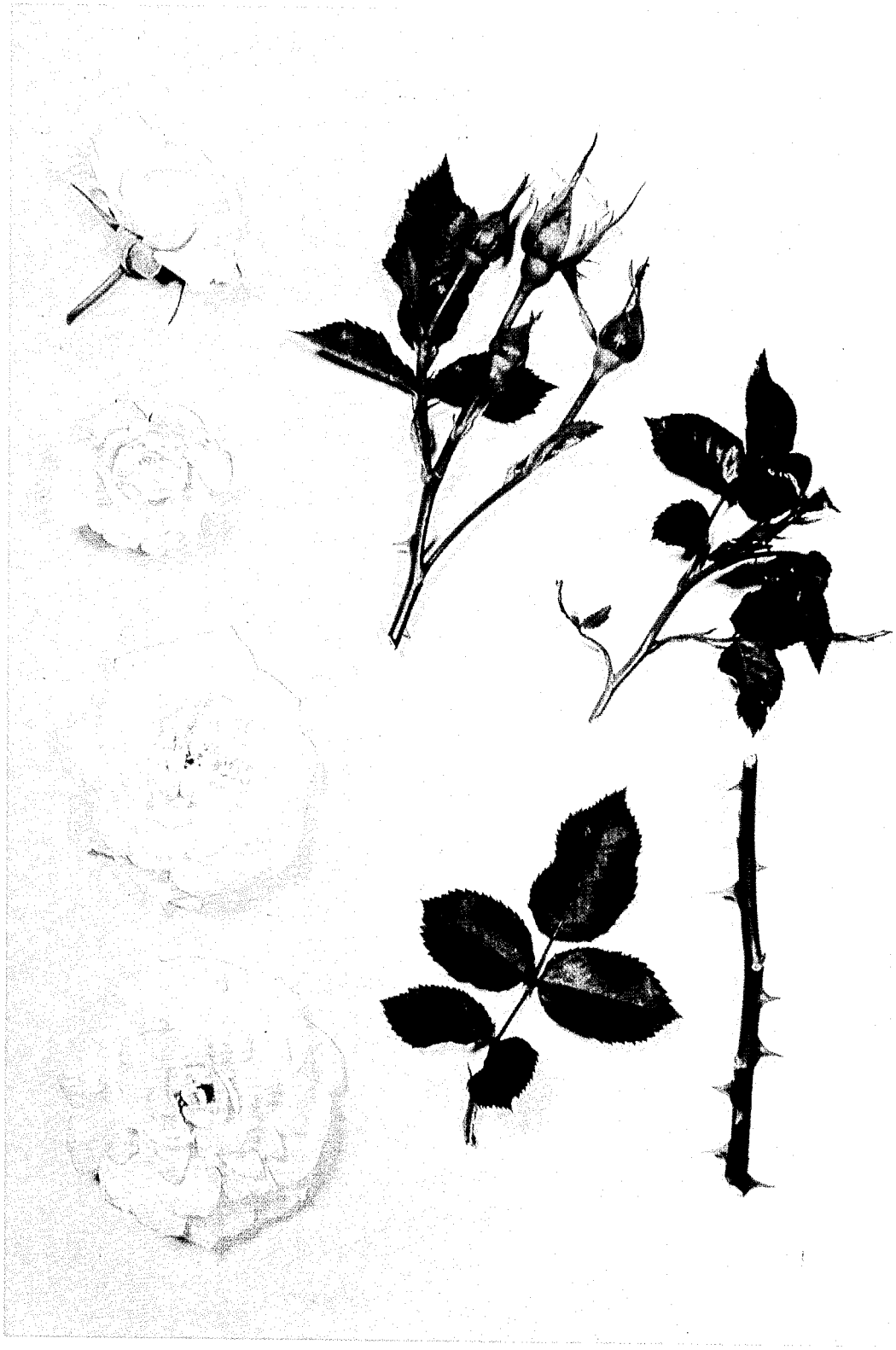

United States Patent Office

Plant Pat. 3,509
Patented Mar. 5, 1974

3,509
ROSE PLANT

Reimer Kordes, Sparrieshoop, near Elmshorn, Germany, assignor to Jackson & Perkins Co., Medford, Oreg.

Filed Sept. 7, 1972, Ser. No. 287,047
Int. Cl. A01h 5/00
U.S. Cl. Plt.—24 1 Claim The present invention relates to a new and distinct variety of rose plant of the floribunda class which was originated by crossing an unnamed seedling variety with the variety Spanish Sun, U.S. Plant Pat. No. 2,809.

The primary objective of this breeding was to produce a rose of the floribunda class having a well shaped plant with good foliage bearing large flowers of a bright yellow color. This objective was fully achieved along with other desirable improvements as evidenced by the following unique combination of characteristics which are outstanding in the new variety and which distinguish if from its parents as well as from all other varieties of which I am aware:

(1) A vigorous habit of growth with many branches originating at the base of the plant.
(2) Bright yellow buds and flowers similar to Wilson's Aureolin, being very much the same color during spring, summer, and autumn.
(3) A strong resistance to rose powdery mildew at Tustin, Calif.
(4) A strong fragrance, similar to its pollen parent, Spanish Sun.
(5) Heavy petal substance.

Asexual reproduction of this new variety by budding, as performed at Sparrieshoop, Germany and Tustin, Calif., shows that the foregoing characteristics and distinctions come true to form and are established and transmitted through succeeding propagations.

The accompanying drawing shows typical specimens of the vegetative growth and flowers of this new variety in different stages of development, depicted in color as nearly true as it is reasonably possible to make the same in a color illustration of this character.

The following is a detailed description of my new rose variety with color terminology in accordance with Wilson's Horticultural Color Chart, except where ordinary dictionary significance of color is indicated.

Parentage: Seedling
*Seed parent.*—Seedling; unnamed.
*Pollen parent.*—Spanish Sun.
Classification:
*Botanic.*—Rosa hybrid.
*Commercial.*—Floribunda.

FLOWER

Observations were made at Tustin, Calif.

Blooming habit: Recurrent—continuous.
Bud:
*Size.*—One inch when petals start to unfurl.
*Form.*—Long, blunt top.
*Color.*—When sepals first divide lemon yellow (4/1). When half blown; inside of petals Aureolin (3), reverse of petals Aureolin (3/1).
*Sepals.* — Color: Outer surface — Lettuce green (861/2). Inner surface—Lettuce green (861/2), covered with white tomentum. Three appendaged sepals normally appendaged. Two unappendaged sepals smooth edged.
*Receptacle.*—Color: Lettuce green (861/3). Shape: Funnel. Size: Broad. Surface: Smooth.
*Peduncle.*—Length: Short. Surface: Mostly smooth, few prickels. Color: Lettuce green (861/3). Strength: Stiff, erect.
*Opening.*—Petal edges undulated without curling back.
Bloom:
*Size.*—Medium, 3 to 3½ inches.
*Borne.*—Singly and in flat clusters.
*Stems.*—Medium.
*Form.*—When first open, high center. Permanence—Retains it form to the end, petal edges undulated.
*Petalage.*—Number of petals under normal conditions 25 to 30.
*Color.*—Center of flower: Upper side of petals Aureolin (3). Reverse side of petals Aureolin (3/1). Outer petals: Upper side and reverse of petals same as center petals. Base of petals: Same. General tonality from a distance Aureolin (3). No variegations.
*Discoloration.*—At end of first day none. Third day lightens to Empire yellow (603).
*Fragrance.*—Strong, similar to Spanish Sun.
Petals:
*Texture.*—Thick.
*Surface.*—Inside—shiny. Reverse—shiny.
*Shape.*—Round.
*Form.*—Undulated.
*Arrangement.*—Imbricated.
*Petaloids in center.*—Few.
*Persistence.*—Drop off cleanly.
*Lastingness.*—On the plant—long. As cut flower—long.
Reproductive parts:
*Stamens, anthers.* — Medium. Color — yellow, Arrangement—regular around styles.
*Stamens, filaments (threads).*—Short. Color—yellow.
*Pollen.*—Golden Yellow.
*Styles.*—Loosely separated, of uneven lengths. Upper part of styles are near Currant Red (821/1).
*Stigmas.*—Color—yellow.
*Ovaries.*—All enclosed in calyx.

PLANT

Form: Bush.
Growth: Vigorous.
Foliage: Number of leaflets on normal mid-stem leaves, 5 to 7, mostly 7.
*Size.*—Medium.
*Quantity.*—Normal.
*Color.*—New foliage: When still folded, same hue as Garnet Brown (00918/3) but much lighter; leaflet edges darker than body of leaflet. Upperside of leaflet is near Pod Green (061/1) overlaid with Garnet Brown (00918/3). Old foliage: Near Parsley Green (00962).
Leaflets:
*Shape.*—Broad, oval.
*Texture.*—Upper side—semi-glossy. Under side—smooth. Ribs and veins—ordinary.
*Edge.*—Serrated, lightly undulated.
*Serration.*—Single, medium sized.
*Petiole (rachis).*—Color—green. Underside—prickles.

Upper side—Hairy along center, small gland-like prickles on side ridges.

*Disease resistance.*—Resistant to mildew under normal growing conditions at Tustin, Calif.

Wood:

*New wood.*—Color—Light green, reddish on side exposed to sun. Bark—Smooth.

*Oldwood.*—Color—Green. Bark—Smooth.

Prickles:

*Quantity.*—On main stalks—ordinary. On laterals—ordinary.

*Form.*—Broad base, long, hooked downward.

*Color.*—When young—reddish (like young foliage) near base.

*Position.*—Irregular.

Small prickles:

*Quantity.*—On main stalks—none except on peduncles. On laterals—none.

I claim:

1. A new and distinct variety of rose plant of the floribunda class, substantially as herein shown and described, characterized particularly as to novelty by the unique combination of excellent, uniform fully branched plant, bright Aureolin Yellow flowers, semi-glossy foliage, heavy petal substance and strong fragrance.

No references cited.

ROBERT E. BAGWILL, Primary Examiner